United States Patent
Park

(10) Patent No.: US 11,123,402 B1
(45) Date of Patent: Sep. 21, 2021

(54) ANTICANCER COMPOSITION COMPRISING CERVICAL CANCER-DERIVED AUTOCRINE MOTILITY FACTOR AS EFFECTIVE COMPONENT

(71) Applicant: DAEGU CATHOLIC UNIVERSITY INDUSTRY ACADEMIC COOPERATION FOUNDATION, Gyeongsangbuk-do (KR)

(72) Inventor: Hee Sung Park, Daegu (KR)

(73) Assignee: DAEGU CATHOLIC UNIVERSITY INDUSTRY ACADEMIC COOPERATION FOUNDATION, Gyeongsangbuk-Do (KR)

( * ) Notice: Subject to any disclaimer, the term of this patent is extended or adjusted under 35 U.S.C. 154(b) by 139 days.

(21) Appl. No.: 16/621,007

(22) PCT Filed: Jun. 4, 2018

(86) PCT No.: PCT/KR2018/006334
§ 371 (c)(1),
(2) Date: Dec. 10, 2019

(87) PCT Pub. No.: WO2018/230874
PCT Pub. Date: Dec. 20, 2018

(30) Foreign Application Priority Data

Jun. 14, 2017 (KR) .................. 10-2017-0074533

(51) Int. Cl.
*A61K 38/52* (2006.01)
*A61K 38/17* (2006.01)
*A61P 35/00* (2006.01)

(52) U.S. Cl.
CPC .......... *A61K 38/1709* (2013.01); *A61P 35/00* (2018.01)

(58) Field of Classification Search
None
See application file for complete search history.

(56) References Cited

U.S. PATENT DOCUMENTS

2003/0223978 A1    12/2003    Nabi

FOREIGN PATENT DOCUMENTS

JP    2004-285057 A    10/2004
KR    10-2016-0050773 A    5/2016

OTHER PUBLICATIONS

Mitra, Aparna et al; "Culture of human cervical cancer cells, siha, in the presence of fibronectin activates mmp-2." J. Canc. Res. Clin. Oncol. (2006) 132 p. 505-513.*
International Search Report for PCT/KR2018/006334 dated Oct. 10, 2018.
NCBI GenBank assession No. ARJ36701.1, Apr. 25, 2017.
Giuseppe Lucarelli et al., "Increased Expression of the Autocrine Motility Factor is Associated With Poor Prognosis in Patients With Clear Cell-Renal Cell Carcinoma", Medicine, vol. 94, No. 46, pp. 1-10, Nov. 2015.
Hahn-Sun Jung et al., "Monoclonal antibodies against autocrine motility factor suppress gastric cancer", Oncology Letteres, vol. 13, No. 6, Apr. 13, 2017.

* cited by examiner

*Primary Examiner* — Fred H Reynolds
(74) *Attorney, Agent, or Firm* — The PL Law Group, PLLC

(57) ABSTRACT

An anticancer composition includes cervical cancer-derived autocrine motility factor (AMF) as an effective component. The cervical cancer-derived AMF has an excellent effect of inhibiting the proliferation of liver cancer, pancreatic cancer, breast cancer, lung cancer, prostate cancer, and colon cancer, and inducing cell death. The composition can be used as an anticancer therapeutic agent.

10 Claims, 9 Drawing Sheets
Specification includes a Sequence Listing.

FIG. 4

```
(A)   1   MAALTRDPQFQKLQQWYREHRSELNLRRLFDANKDRFNHFSLTLNTNHGHILVDYSKNLV
(B)   1   MAALTRDPQFQKLQQWYREHRSELNLRRLFDANKDRFNHFSLTLNTNHGHILVDYSKNLV
          ************************************************************

(A)  61   TEDVMRMLVDLAKSRGVEAARERMFNGEKINYTEGRAVLHVALRNRSNTPILVDGKDVMP
(B)  61   TEDVMRMLVDLAKSRGVEAARERMFNGEKINYTEGRAVLHVALRNRSNTPILVDGKDVMP
          ************************************************************

(A) 121   EVNKVLDKMKSFCQRVRSGDWKGYTGKTITDVINIGIGGSDLGPLMVTEALKPYSSGGPR
(B) 121   EVNKVLDKMKSFCQRVRSGDWKGYTGKTITDVINIGIGGSDLGPLMVTEALKPYSSGGPR
          ************************************************************

(A) 181   VWYVSNIDGTHIAKTLAQLNPESSLFIIASKTFTTQETITNAETAKEWFLQAAKDPSAVA
(B) 181   VWYVSNIDGTHIAKTLAQLNPESSLFIIASKTFTTQETITNAETAKEWFLQAAKDPSAVA
          ************************************************************

(A) 241   KHFVALSTNTTKVKEFGIDPQNMFEFWDWVGGRYSLWSAIGLSIALHVGFDNFEQLLSGA
(B) 241   KHFVALSTNTTKVKEFGIDPQNMFEFWDWVGGRYSLWSAIGLSIAWHVGFDNFEQLLSGA
          ******************************************** ***************

(A) 301   HWMDQHFRTTPLEKNAPVLLALLGIWYINC-FGCETHAMLPYDQYLHRFAAYFQQGDMES
(B) 301   HWMDHHFRTTPLEKNAPVLLALLGIWYINCLWGCETHAMLPYDQYLQRFAAYFQQGDLES
          **** ************************* *************** ********** **

(A) 360   NGKYITKSGTRVDHQTGPIVWGEPGTNGQHAFYQLIHQGTKMIPCDFLIPVQTQHPIRKG
(B) 361   NGKYITKSGTRVDHQTGPIVWGEPGTNGQHAFYQLIHQGTKMIPCDFLIPVQTQHPIRKG
          ************************************************************

(A) 420   LHHKILLANFLAQTEALMRGKSTEEARKELQAAGKSPEDLERLLPHKVFEGNRPTNSIVF
(B) 421   LHHKILLANFLAQTEALMRGKSTEEARKELQAAGKSPEDLERLLPHKVFEGNRPTNSIVF
          ************************************************************

(A) 480   TKLTPFMLGALVAMYEHKIFVQGIIWDINSFDQWGVELGKQLAKKIEPELDGSAQVTSHD
(B) 481   TKLTPFMLGALVAMYEHKIFVQGIIWDINSFDQWGVELGKQLAKKIEPELDGSAQVTSHD
          ************************************************************

(A) 540   ASTNGLINFIKQQREARVQ   (SEQ ID NO: 4)
(B) 541   ASTNGLINFIKQQREARVQ   (SEQ ID NO: 1)
          *******************
```

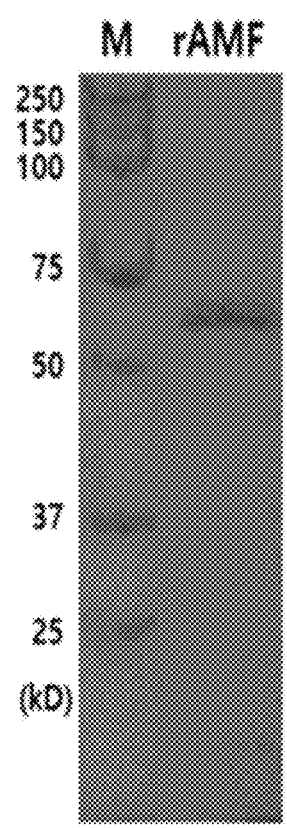

ANTICANCER COMPOSITION COMPRISING CERVICAL CANCER-DERIVED AUTOCRINE MOTILITY FACTOR AS EFFECTIVE COMPONENT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2018/006334, filed on Jun. 4, 2018, which claims priority to the benefit of Korean Patent Application No. 10-2017-0074533 filed in the Korean Intellectual Property Office on Jun. 14, 2017, the entire contents of which are incorporated herein by reference.

TECHNICAL FIELD

The present invention relates to an anticancer composition comprising cervical cancer-derived autocrine motility factor as an effective component, and, more specifically, it relates to an anticancer pharmaceutical composition comprising cervical cancer-derived autocrine motility factor as an effective component that can exhibit an anticancer effect for liver cancer, pancreatic cancer, breast cancer, lung cancer, prostate cancer, and colon cancer.

BACKGROUND ART

With infection diseases and cardiovascular diseases, cancer is one of the three most important causes of morbidity all over the world, and, due to the environmental problems, longer life expectancy, westernized diet, or the like, it is expected that population having cancer dramatically increases in future. In spite that many studies have been made on cancer to develop a more effective anticancer agent, due to diversified onset mechanisms of cancer, development of a new anticancer agent having less side effect and resolving the problems associated with resistance is still strongly desired.

Meanwhile, cell competition is a comparative process between growth adaptation and survival among cells, and the cells lagging behind the competition may not survive. Cell competition is closely related with an onset of cancer, and peripheral cells having poorer growth adaptability than cancer cells may disappear. Until now, it has been assumed that the cells winning the competition (i.e., winner cells) secret a cell death signal at the early stage of cell competition, but it remains still unclear.

Meanwhile, autocrine motility factor (AMF) is known, as a housekeeping protein related to the energy metabolism in cells, to play the role of interconverting glucose-6-phosphate and fructose-6-phosphate of the second process of glycolysis, and, due to such function, it is also referred to as glucose-6-phosphate isomerase (GPI). AMF as a cytokine secreted from tumor is present in large amount in an area with tumor, and it plays a key role in proliferation, differentiation, and survival of tumor.

Meanwhile, in Korean Patent Application Publication No. 2016-0050773, AMFR-Fc fusion protein and anticancer use thereof are disclosed. However, the anticancer composition comprising cancer cell-derived AMF as an effective component has not been disclosed before.

SUMMARY

The present invention is devised under the circumstances described in the above, and, by providing an anticancer composition comprising cervical cancer-derived AMF as an effective component, and confirming that the composition inhibits a certain type of cancer, specifically, liver cancer, pancreatic cancer, breast cancer, lung cancer, prostate cancer, and colon cancer, and causes cell death, the inventors completed the present invention.

To solve the aforementioned problems, the present invention provides an anticancer pharmaceutical composition comprising cervical cancer-derived AMF as an effective component.

The present invention relates to an anticancer composition comprising cervical cancer-derived AMF as an effective component, and, as the cervical cancer-derived AMF of the present invention has an excellent effect of inhibiting the proliferation of liver cancer, pancreatic cancer, breast cancer, lung cancer, prostate cancer, and colon cancer and also causing the cell death, the composition of the present invention comprising cervical cancer-derived AMF as an effective component can be used as a material for anticancer therapy.

BRIEF DESCRIPTION OF THE DRAWINGS

FIG. 4 shows the result of comparing the amino acid sequence of recombinant AMF derived from cervical cancer with the amino acid sequence of GPI isoform protein (Genbank accession number: BC004982.1), in which (A) is the amino acid sequence of GPI isoform protein and (B) is the amino acid sequence of recombinant AMF derived from cervical cancer. * indicates that (A) and (B) have the same sequence.

FIGS. 5A to 5C show the result of purifying recombinant AMF derived from cervical cancer, monitoring with a microscope the death of cancer cells caused by the purified recombinant AMF derived from cervical cancer, and counting the cell number, in which rAMF represents the recombinant AMF derived from cervical cancer, A549 represents lung cancer cells, and AsPC-1 represents pancreatic cancer cells.

DETAILED DESCRIPTION

Figure 1:
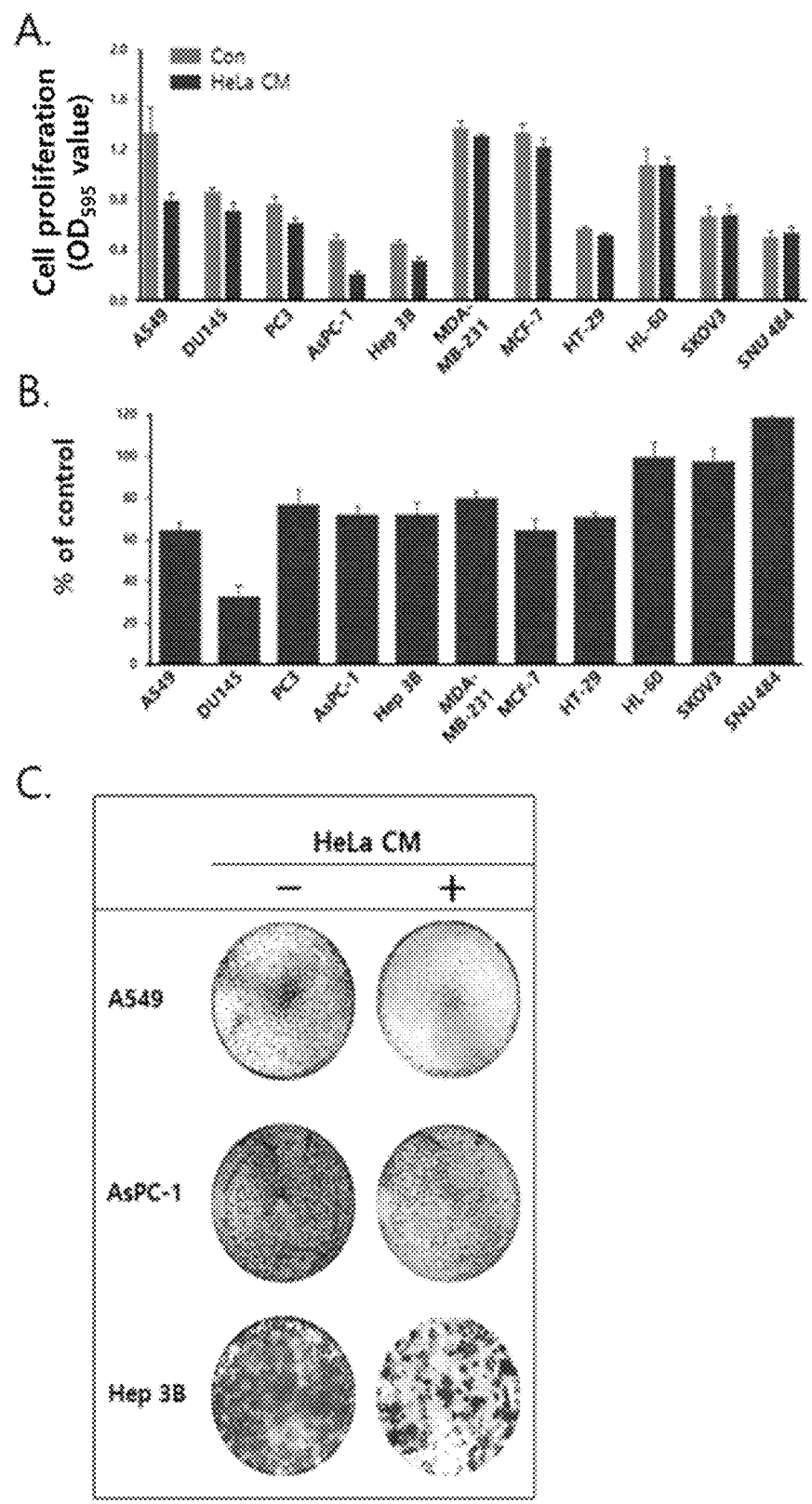
FIG. 1 shows the result of determining the proliferation of cancer cells when conditioned medium (CM) of cervical cancer cells is used for the treatment of other cancer cell line, in which the determination is made based on MTT analysis, cell counting, or colony formation. A549 represents lung cancer cell line, DU145 and PC3 represent prostate cancer cell line, AsPC-1 represents pancreatic cancer cell line, Hep3B represents liver cancer cell line, MDA-MB-231 and MCF-7 represent breast cancer cell line, HT-29 represents colon cancer cell line, HL-60 represents leukemia cell line, SKOV3 represents ovarian cancer cell line, and SNU 484 represents stomach cancer cell line.

The present invention relates to an anticancer pharmaceutical composition comprising cervical cancer-derived AMF as an effective component.

The cervical cancer-derived AMF consists of the amino acid sequence of SEQ ID NO: 1. Functional equivalents of the protein having the amino acid sequence of SEQ ID NO: 1 also fall within the scope of the cervical cancer-derived AMF of the present invention. The term "functional equivalents" indicates a protein having, as a result of addition, substitution, or deletion of an amino acid, at least 70%, preferably at least 80%, more preferably at least 90%, and even more preferably at least 95% sequence homology with the amino acid sequence represented by SEQ ID NO: 1, and it indicates a protein exhibiting substantially the same activity as the protein represented by SEQ ID NO: 1. A peptide exhibiting substantially the same activity as the cervical cancer-derived AMF is also included. The expression "substantially the same activity" means an activity for prophylaxis or treatment of cancer.

As described herein, the anticancer means inhibition of the proliferation of cancer cells or killing cancer cells, and the composition of the present invention may exhibit the anticancer activity for at least one selected from the group consisting of liver cancer, pancreatic cancer, breast cancer, lung cancer, prostate cancer, and colon cancer, but it is not limited thereto.

The anticancer pharmaceutical composition according to one embodiment of the present invention may inhibit the cancer cell proliferation and induce the cancer cell death, but it is not limited thereto.

The pharmaceutical composition according to the present invention may be used after it is formulated into an oral formulation such as capsule, powder, granule, tablet, suspension, emulsion, syrup, or aerosol, a formulation for external application, a suppository, or a sterile injection solution.

As for the carrier, vehicle, and diluent which may be contained in the pharmaceutical composition of the present invention, various kinds of compounds and mixtures including lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, mineral oil, or the like can be mentioned.

At the time of preparing a formulation, the preparation is produced by using a diluent or a vehicle like filler, bulking agent, binding agent, wetting agent, disintegrating agent, or surfactant that are commonly used. Included in the solid preparation for oral administration are a tablet, a pill, a powder, a granule, and a capsule, and the solid preparation is prepared by mixing the aforementioned pharmaceutical composition with at least one vehicle, for example, starch, calcium carbonate, sucrose, lactose, gelatin, or the like. Furthermore, other than a simple vehicle, a lubricating agent such as magnesium stearate or talc is also used. Examples of a liquid preparation for oral administration include a suspension, a solution, an emulsion, and a syrup, and, other than water, liquid paraffin or the like that are commonly used as a simple diluent, various kinds of a vehicle such as wetting agent, sweetening agent, aroma, preservative or the like may be included. Included in the preparation for parenteral administration are a sterilized aqueous solution, a non-aqueous solvent, a suspension agent, an emulsifying agent, a freeze-dry preparation, and a suppository. As the non-aqueous solvent or suspension agent, plant oil such as propylene glycol, polyethylene glycol, or olive oil, and injectable ester like ethyloate can be used. As a base of a suppository, witepsol, macrogol, Tween 61, cacao fat, laurin fat, glycerol gelatin, or the like can be used.

Suitable dosage of the pharmaceutical composition of the present invention can be decided differently depending on various factors including a method for preparing the formulation, administration mode, age, bodyweight, sex, conditions, and diet of a patient, administration time, administration route, excretion rate, and response sensitivity.

The pharmaceutical composition of the present invention can be administered either orally or parenterally, and, in case of parenteral administration, the administration can be made by topical application on skin, intravenous injection, subcutaneous injection, intramuscular injection, intraperitoneal injection, or transdermal administration.

The present invention also provides a method for inhibiting the cell proliferation or promoting the cell death of cancer cells comprising administering the aforementioned anticancer pharmaceutical composition to a mammal other than human.

Hereinbelow, the present invention is explained in greater detail in view of the Examples. However, the Examples are given only for more specific explanation of the present invention, and it is evident for a person who has common knowledge in the pertinent art that the scope of the present invention is not limited by the Examples.

Materials and Methods

1. Cell Culture

Human cancer cell line used for the present experiment was purchased from Korean Cell Line Bank (Seoul, Korea). HeLa as cervical cancer cell, AsPC-1 as pancreatic cancer cell, MCF-7 and MDA-MB-22 as breast cancer cell, A549 as lung cancer cell, PC3 and DU145 as prostate cancer cell, HL-60 as leukemia cell, SKOV3 as ovarian cancer cell, HT-29 as colon cancer cell, and SNU 484 as stomach cancer cell were cultured at conditions of 37° C., 5% $CO_2$ in DMEM medium containing 10% fetal bovine serum (FBS), 100 U/ml of penicillin G, and 100 µg/ml of streptomycin.

2. Preparation of Serum-Free Conditioned Medium (CM)

When each cancer cell line has grown to a ratio of 80% or so in 75 $cm^2$ culture flask, it was washed 3 times with phosphate-buffered saline (PBS), and then the medium was replaced with a serum-free medium. The serum-free medium was collected 24 hours later, and, after filtering through a 0.22 µm filter, it was stored at −20° C.

In the same manner as above, HeLa cells were prepared by culture in 175 cm² culture flask, and, after washing with PBS, the medium was replaced with a fresh serum-free medium and the cells were cultured for 24 hour to obtain the serum-free conditioned medium (hereinafter, CM). After that, the serum-free conditioned medium was collected for 72 hours with an interval of 24 hours so that HeLa CM was obtained in total amount of 5l. The HeLa CM was filtered through a 0.22 μm filter, and then stored at −20° C.

3. Analysis of Cell Growth

Cells were cultured for 24 hours in a 24-well culture dish, and, after treating the cultured cells with the HeLa CM, the cells were cultured again for 48 hours to 72 hours.

Cell growth was observed at the wavelength of 570 nm based on MTT (3-[4,5-dimethylthiazol-2-yl]-2,5-diphenyltetrazolium bromide; thiazolyl blue) analysis.

Furthermore, to determine the viable cell count, trypan blue exclusion assay was carried out.

Furthermore, for clonogenic assay, the cells were inoculated to a 24-well culture dish, cultured for 12 hours at 37° C., and, after treating the cultured cells with 5% (v/v) HeLa CM, further cultured until colony is formed. Once the colony is formed, washing with PBS was carried out followed by fixing for 5 minutes with 100% methanol. Then, after staining for 2 hours with 0.5% (w/v) Crystal Violet, observation was made after impregnation in distilled water.

4. Protein Purification Identification

Freeze-dried HeLa CM was dissolved in Tris buffer (50 mM Tris-HCl, pH 7.5) and dialyzed against the same buffer at 4° C. After the dialysis, HeLa CM sample was loaded onto a column containing 30 ml of diethylaminoethyl (DEAE) sepharose which has been pre-equilibrated with Tris buffer solution. The bound protein was eluted from the column by using linear gradient of 0 M to 1.0 M sodium chloride (NaCl) in Tris buffer at flow rate of 0.7 ml per minute. The eluted fractions containing major peaks with biological activity were collected, and, according to dialysis against sucrose, the fractions were concentrated in a dialysis tube (7000 MWCO). The concentrated sample was fractionated again by using a column filled with 0.8×30 cm Sephacryl S-200, which has been pre-equilibrated with Tris buffer solution. The physiologically active fractions were collected at a flow rate of 0.1 ml/minute, and then concentrated by dialysis as described in the above. The physiological activity was evaluated by analysis of A549 cell growth by using trypan blue exclusion assay, and size of the sample exhibiting the physiological activity was determined by 12% SDS-PAGE gel. Thereafter, to have the protein identification, MALDI-TOF mass analysis was carried out.

5. AMF Blocking Assay

After culturing the cells for 2 days with or without a treatment using HeLa CM, HeLa CM containing 0.5 mM E4P (inhibitor for AMF activity) or IP-HeLa CM from which AMF has been removed by immunoprecipitation (IP), the viable cell count was determined. For preparing the IP-HeLa CM, 1 ml of HeLa CM was cultured with 1 μg of anti-GPI/AMF for 1 hour, and then treated for 1 hour with 1 μl of protein A/G agarose bead. After that, to remove the beads on which the antigen-antibody complex is bound, centrifuge was carried out for 2 minutes and 3000 rpm.

6. DNA Cloning and Expression of Recombinant Protein

HeLa cDNA library (B-Bridge Co., Tokyo, Japan) was used as a template for amplifying AMF cDNA by PCR (30 seconds at 95° C., 30 seconds at 58° C. and 100 seconds at 72° C., repeating 30 times this cycle).

The forward primer including NdeI restriction enzyme site and the reverse primer including XhoI restriction enzyme site were prepared based on the DNA sequence encoding GPI (Genbank accession number: AK301103.1).

Forward primer: 5'-TACATATGGCCGCTCT-CACCCGG-3' (SEQ ID NO: 2)

Reverse primer: 5'-GCAGCGCGAGGCCAGAGTC-CAACTCGAG-3' (SEQ ID NO: 3)

Sequence of the PCR product with length of 1.7 kb was determined, and, according to cloning in pET-21b vector, pHeLa-AMF was constructed. E. coli BL21 containing pHeLa-AMF was cultured for 16 hours on a LB medium containing 200 μg/ml ampicillin at conditions including 200 rpm and 37° C. followed by dilution at 1:100 with a fresh medium. Then, E. coli BL21 was cultured again for 3 hours at conditions including 200 rpm and 37° C. After that, the cells were treated with 0.5 mM IPTG, and cultured for 16 hours at conditions including 100 rpm and 20° C. The collected cells were re-suspended in a buffer solution (20 mM Tris-HCl pH 8.0, 200 mM NaCl, 1 mM DTT and 0.5 mM PMSF) containing 1 mg/ml lysozyme, and then reacted for 30 minutes on ice. After the reaction, the cells were disrupted by using a French pressure cell press (Model FA-078A, Thermo IEC, Milford, Mass., USA), and, according to centrifuge for 20 minutes at conditions including 12000 rpm and 4° C., lysed fractions were obtained. The obtained fractions were passed through a 0.22 μm injection filter. According to the protocol provided by a supplier, HeLa recombinant AMF (HeLa rAMF) was purified by using His60 Ni resin affinity chromatography (Promega, Madison, Wis., USA). The purified protein sample was further purified by using Sephacryl S-200 chromatography which has been pre-equilibrated with 20 mM Tris-HCl and 50 mM sodium chloride (NaCl). The protein content was quantified by using Bio-Rad protein analysis reagents.

7. Protein Extraction and Western Blot

The cells were detached from culture dish by using a rubber scraper, and, after collecting by centrifuge (3000 rpm, 5 minutes), washed twice with PBS. The cell pellet was allowed to float in cold RIPA buffer solution (50 mM Tris-HCl pH7.4, 1% NP-40, 0.5% Na-deoxycholate, 0.1% SDS, 150 mM NaCl, 2 mM EDTA, 50 mM NaF) containing protease inhibition cocktail, and reacted for 30 minutes on ice for cell lysis. The mixture after the reaction was centrifuged (13000 rpm, 20 minutes, 4° C.) to give a clear lysate. Then, the protein was loaded, in the same amount for each sample, and separated by 12% SDS-PAGE followed by transfer onto a PVDF membrane. The protein bound to the membrane was subjected to Western blot analysis by using ECL system.

Example 1. Inhibitory Effect of HeLa CM on Cancer Cell Proliferation

To determine the inhibitory effect of HeLa CM on cancer cell proliferation, various cancer cells other than cervical cancer cells were treated with HeLa CM, and then MTT analysis, trypan blue exclusion analysis, and clonogenic assay were carried out. As a result, as it is shown in FIG. 1, it was confirmed that the cell proliferation was inhibited in liver cancer (Hep3B), pancreatic cancer (AsPC-1), breast cancer (MDA-MB-231, MCF-7), lung cancer (A549), prostate cancer (DU145, PC3), and colon cancer (HT-29) which have been treated with CM of HeLa as cervical cancer-derived cells. However, it was also confirmed that no influence is exhibited on cell proliferation of leukemia (HL60), ovarian cancer (SKOV3), and stomach cancer (SNU 484), or rather the effect of promoting the proliferation thereof was shown.

Based on this result, it was confirmed that HeLa CM specifically inhibits the cell proliferation of liver cancer (Hep3B), pancreatic cancer (AsPC-1), breast cancer (MDA-MB-231, MCF-7), lung cancer (A549), prostate cancer (DU145, PC3), and colon cancer (HT-29).

Example 2. Analysis of HeLa Secreting Protein

Figure 2A:
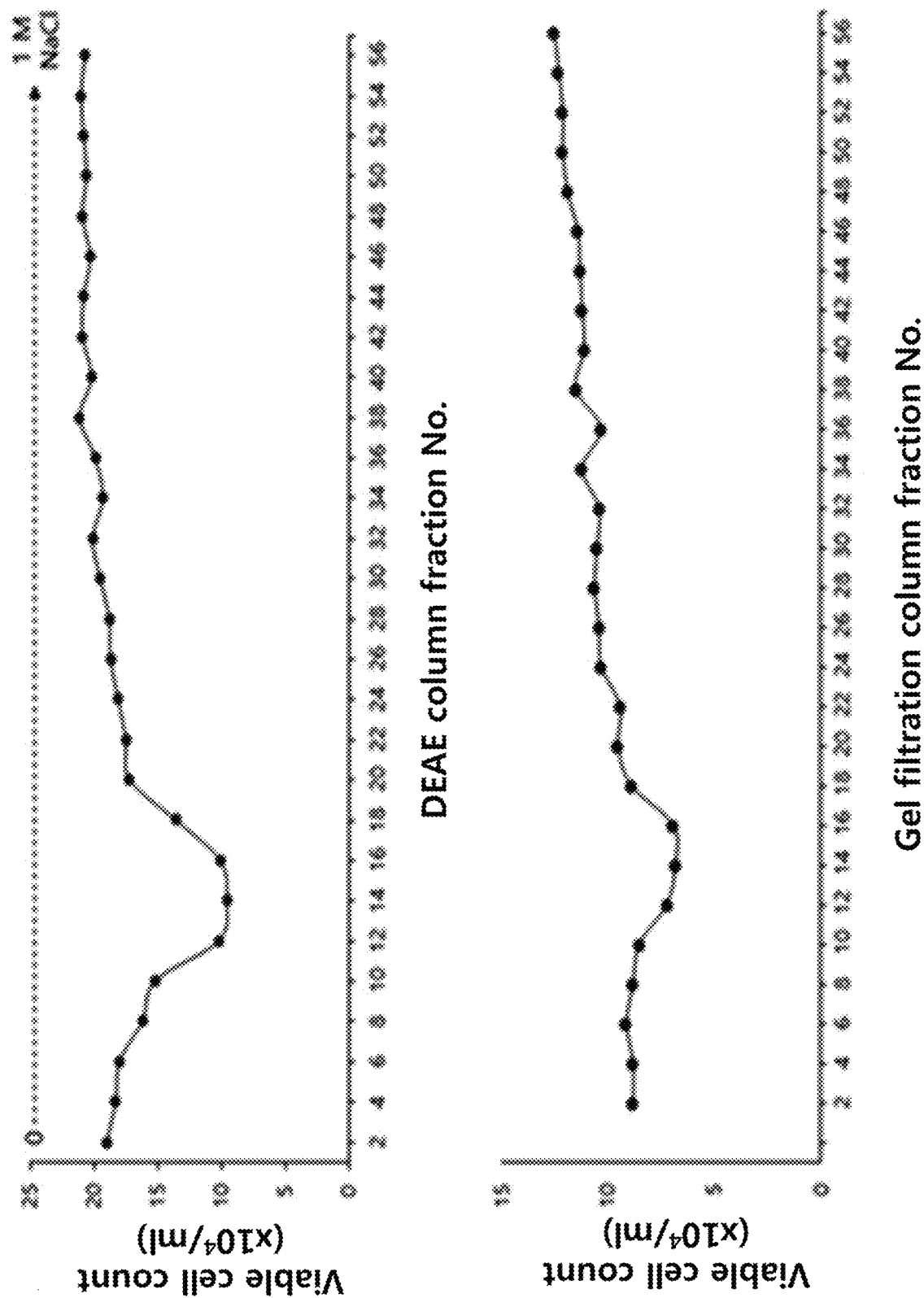
FIGS. 2A and 2B show the result of determining the degree of cell proliferation when DEAD column fractions of the conditioned medium of cervical cancer cells and fractions exhibiting the physiological activity among the DEAE column fractions are fractionated again by a gel filter column, and cancer cells are treated with the resulting fractions, and determining three proteins (moesin, transketolase, and AMF) from the fraction with most inhibited cell proliferation. 1 M NaCl means that the physiologically active materials are fractionated by increasing the NaCl concentration from 0 M to 1 M, and S-200 represents the physiologically active fraction of gel filter chromatography.
Figure 2B:
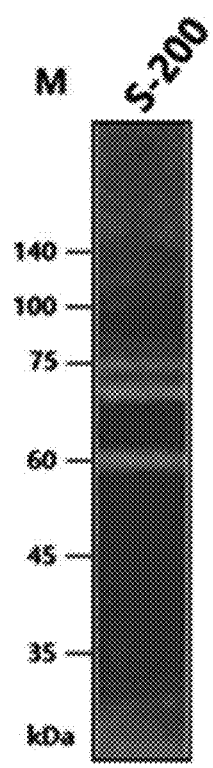

To analyze the protein that is included in HeLa CM and exhibits the inhibitory effect on proliferation of cancer cells, protein purification and identification was carried out. As shown in FIG. 2A, the DEAE sepharose fractions and fractions exhibiting the physiological activity among the DEAE sepharose fractions were fractionated again by using a column filled with Sephacryl S-200, and the fractions exhibiting an excellent physiological activity were determined from the fractions obtained after the re-fractionation. The physiological activity was determined based on inhibition of the proliferation of cancer cells after treating A549 cells with the fractions. Furthermore, from the fractions exhibiting an excellent physiological activity as shown in FIG. 2B, proteins with a size of 75, 70 and 60 kDa were confirmed, and, as a result of performing the mass analysis using MALDI-TOF, the three proteins were found to be moesin, transketolase, and AMF, respectively. Moesin is an extension spike protein constituting a cell membrane, transketolase is an enzyme which plays a key role in pentose phosphate cycle, and AMF is a protein related to the mobility and proliferation of cancer cells. Among them, AMF being related to cancer cells and a secretory protein was selected and used for carrying out the following experiments.

Example 3. Inhibitory Effect on AMF Activity

Figure 3:
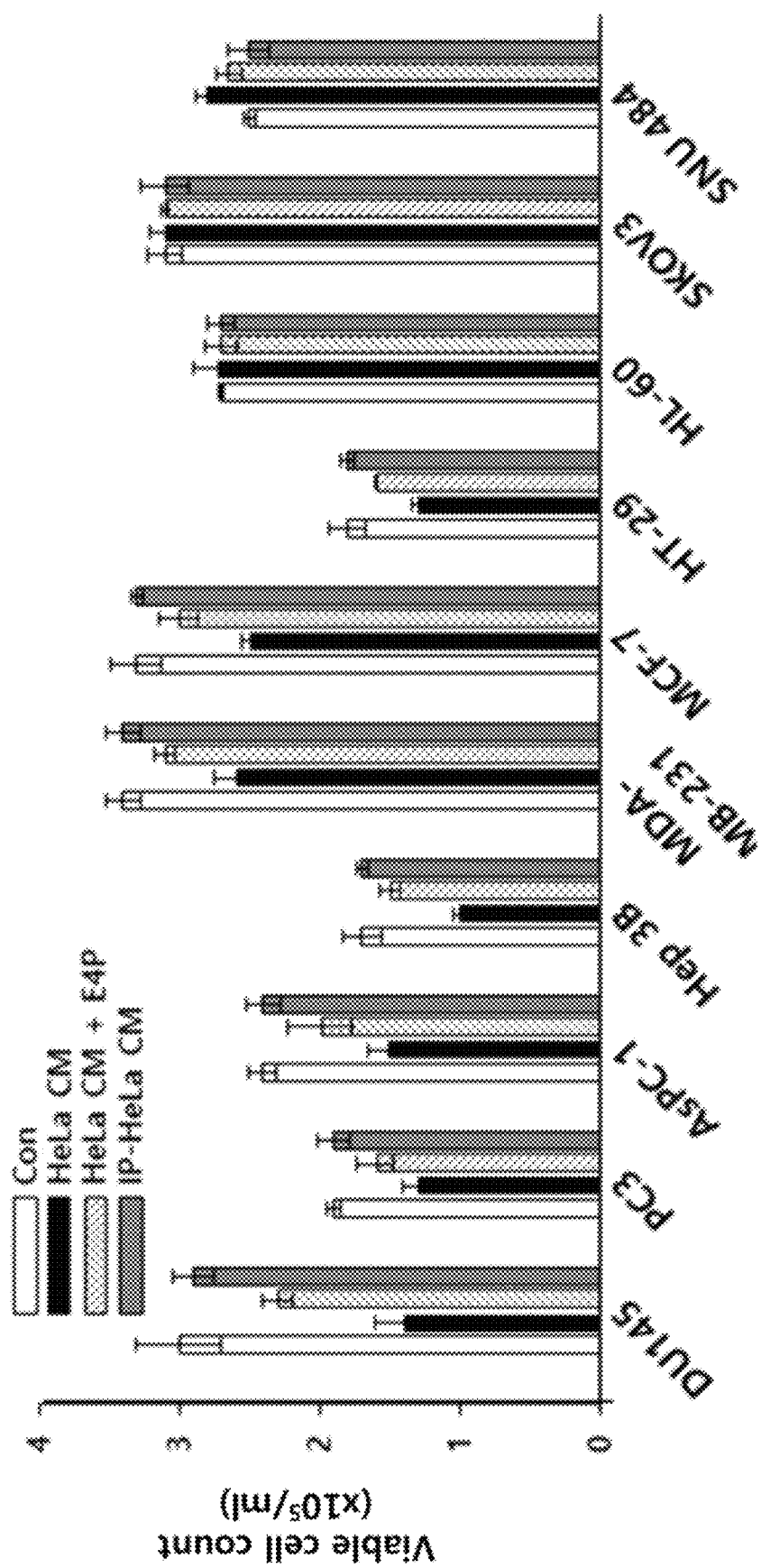
FIG. 3 shows the result of confirming that the effect of inhibiting cell proliferation by conditioned medium of cervical cancer cells is caused by AMF. Con represents a negative control, HeLa CM represents a conditioned medium of cervical cancer cells, HeLa CM+E4P represents a group in which the conditioned medium of cervical cancer cells is treated with an AMF activity inhibitor, and IP-HeLa CM represents conditioned medium of cervical cancer cells from which AMF has been removed by using an AMF antibody. DU145 and PC3 represent prostate cancer cell line, AsPC-1 represents pancreatic cancer cell line, Hep3B represents liver cancer cell line, MDA-MB-231 and MCF-7 represent breast cancer cell line, HT-29 represents colon cancer cell line, HL-60 represents leukemia cell line, SKOV3 represents ovarian cancer cell line, and SNU 484 represents stomach cancer cell line.

To determine whether AMF present in HeLa CM can inhibit the cell proliferation or not, the AMF blocking assay was carried out. As a result, as it is shown in FIG. 3, when HeLa CM is treated with E4P, which is a substance for inhibiting the activity of AMF, i.e., HeLa CM+E4P, or the AMF in HeLa CM is removed in advance by using an AMF antibody, i.e., IP-HeLa CM, the proliferation inhibitory effect on liver cancer (Hep3B), pancreatic cancer (AsPC-1), breast cancer (MDA-MB-231, MCF-7), prostate cancer (DU145, PC3), colon cancer (HT-29), which has been caused by HeLa CM, was restored. Based on this result, it was confirmed that the AMF in HeLa CM exhibits the inhibitory effect on proliferation of specific cancer cells.

Example 4. Structure Analysis of HeLa-Derived AMF Gene

After amplifying HeLa AMF cDNA by using HeLa cDNA library, cloning into pET-21b vector was carried out to construct pHeLa-AMF. As a result of analyzing the amino acid sequence of the recombinant AMF, which has been produced by using pHeLa-AMF, it was found to have the homology of 98.9% with GPI isoform protein (Genbank accession number: BC004982). However, there were several mutations as shown in FIG. 4.

Figure 5B:
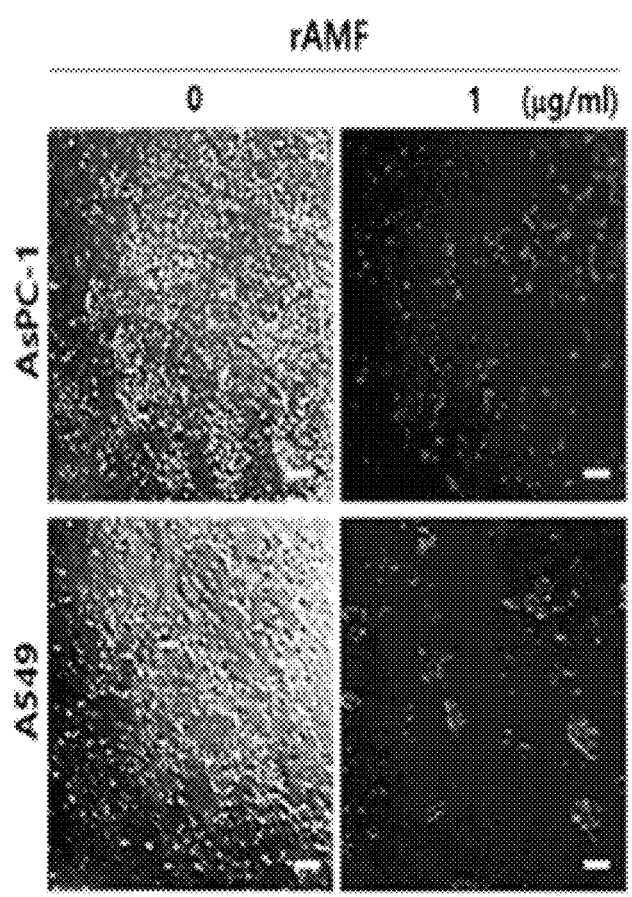
Figure 5C:
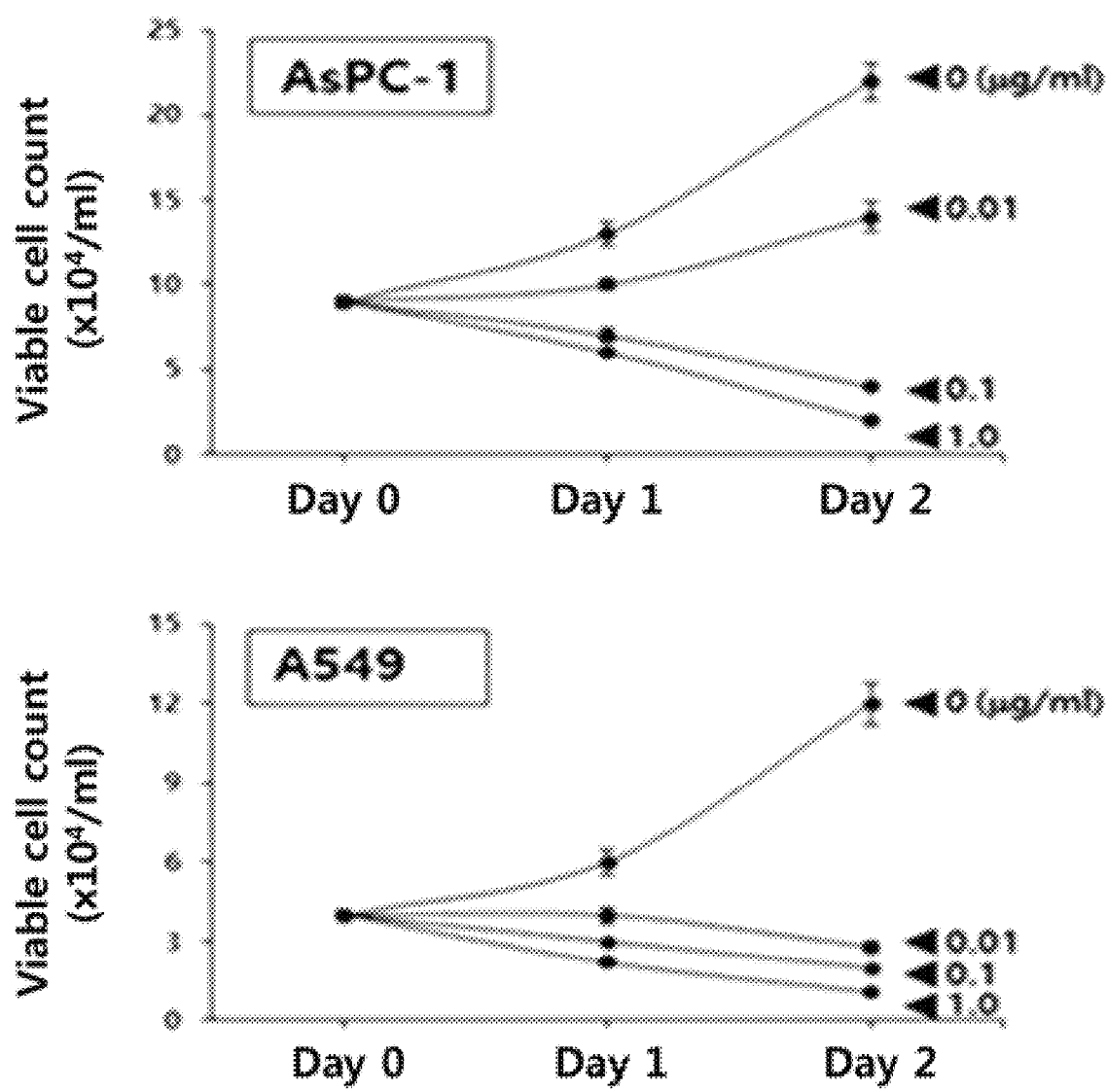

Example 5. Inhibitory Effect of HeLa-Derived Recombinant AMF on Cell Proliferation The recombinant AMF purified as shown in FIG. 5A was confirmed, and then cancer cells were treated therewith to examine the effect exhibited on cell proliferation. As a result, as it is shown in FIG. 5B, the effect of inhibiting cell proliferation is shown when AsPC-1 or A549 cancer cells are treated with 1 µg/ml recombinant AMF. Furthermore, as shown in FIG. 5C, it was found that, compared to the no-treatment control group, the cell proliferation was inhibited in concentration dependent manner when the cells are treated with the recombinant AMF at various concentrations (0.01, 0.1 and 1 µg/ml).

Figure 6:
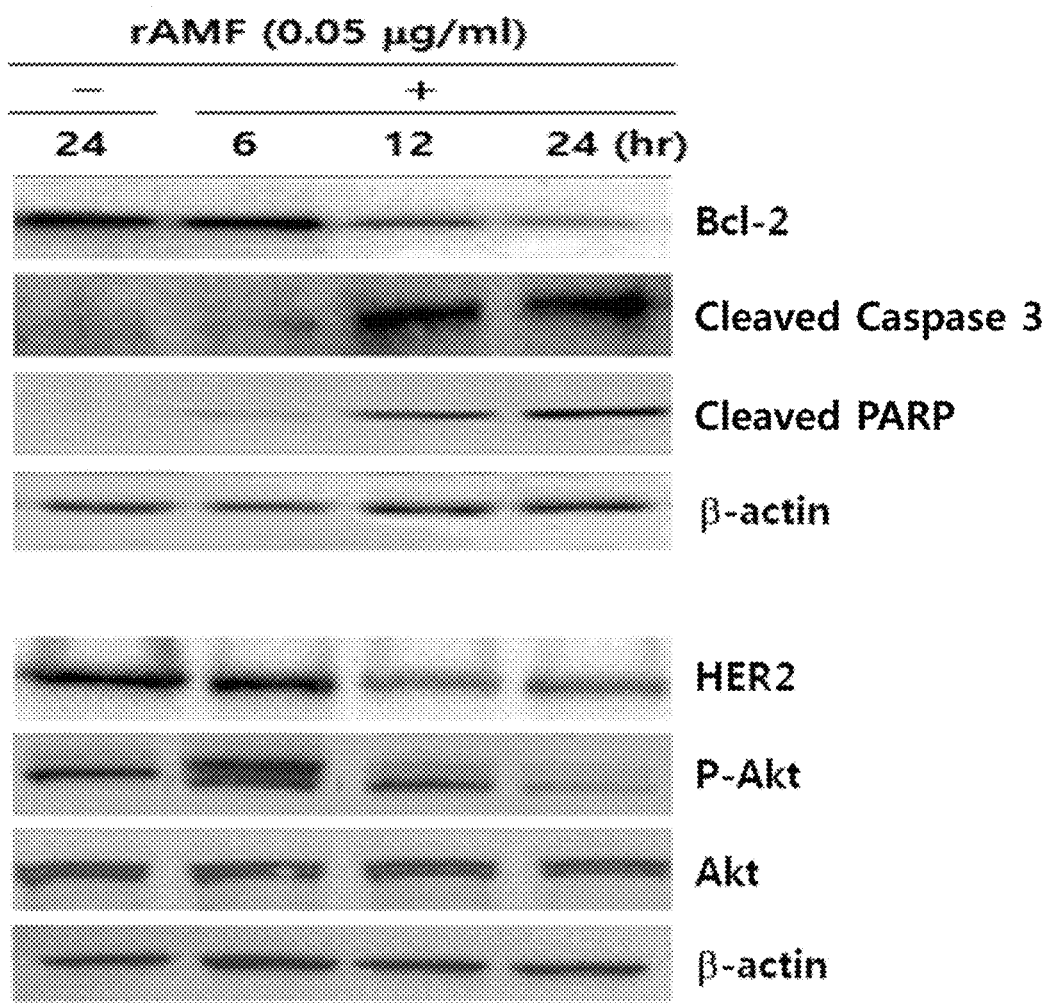
FIG. 6 shows the result of confirming the cell death as the recombinant AMF derived from cervical cancer acts as an antagonist of HER2, in which rAMF represents the recombinant AMF derived from cervical cancer, and A549 cancer cells are used.

Example 6. Change in Expression of Cell Death-Related Factors Caused by HeLa-Derived Recombinant AMF A549 cells were treated with the recombinant AMF for different time period (i.e., 6 hours, 12 hours, or 24 hours), and then the change in expression of cell death-related factors was determined. As a result, as it is shown in FIG. 6, it was found that the expression of anti-cell death factor Bcl-2 has decreased over time when treated with the recombinant AMF. Furthermore, it was also found that the expression of cleaved caspase-3 and cleaved PARP as a cell death factor has increased.

Since AMF is known to regulate the proliferation of cancer cells and angiogenesis as it binds to an AMF receptor to participate in intracellular PI3K/AKT signal transduction, and also promote the growth of cancer cells as it binds to HER2, the influence of the recombinant AMF exhibited on phosphorylation of HER2 and AKT was examined. As the phosphorylation of HER2 and AKT was reduced by a treatment with the recombinant AMF, it was confirmed that HER2 expression in cancer cells is inhibited and AMF can function as an antagonist for HER2 if a treatment is carried out with a recombinant AMF which is different from the AMF secreted by itself.

A sequence listing electronically submitted with the present application on Dec. 10, 2019 as an ASCII text file named 20191210_Q22719GR12_TU_SEQ, created on Dec. 10, 2019 and having a size of 11,000 bytes, is incorporated herein by reference in its entirety.

The invention claimed is:

1. A method for inhibiting proliferation of cancer cells or promoting death of the cancer cells, the method comprising administering a pharmaceutical composition comprising cervical cancer-derived autocrine motility factor (AMF) with the amino acid sequence represented by SEQ ID NO:1 to a subject having the cancer cells, wherein the cancer cells are cells of at least one cancer selected from the group consisting of liver cancer, pancreatic cancer, breast cancer, lung cancer, prostate cancer, and colon cancer.

2. The method of claim 1, wherein the method is for inhibiting the proliferation of the cancer cells.

3. The method of claim 1, wherein the method is for promoting the death of the cancer cells.

4. The method of claim 1, wherein the pharmaceutical composition is prepared in the form of a capsule, a powder, a granule, a tablet, a suspension, an emulsion, a syrup, an aerosol, a formulation for external application, a suppository, or a sterile injection solution.

5. The method of claim 1, wherein the subject is a human.

6. The method of claim 1, wherein the subject is a mammal other than human.

7. A method of treating cancer in a subject, comprising administering to the subject a composition comprising a cervical cancer-derived autocrine motility factor (AMF) with SEQ ID NO:1 wherein the cancer is selected from the group consisting of liver cancer, pancreatic cancer, breast cancer, lung cancer, prostate cancer, colon cancer, or a combination thereof.

8. The method of claim 7, wherein the composition is prepared in the form of a capsule, a powder, a granule, a tablet, a suspension, an emulsion, a syrup, an aerosol, a formulation for external application, a suppository, or a sterile injection solution.

9. The method of claim 7, wherein the subject is a human.

10. The method of claim 7, wherein the subject is a mammal other than human.

* * * * *

SEQUENCE LISTING

```
<160> NUMBER OF SEQ ID NOS: 4

<210> SEQ ID NO 1
<211> LENGTH: 559
<212> TYPE: PRT
<213> ORGANISM: Artificial Sequence
<220> FEATURE:
<223> OTHER INFORMATION: cervical cancer-derived AMF

<400> SEQUENCE: 1
```

```
Met Ala Ala Leu Thr Arg Asp Pro Gln Phe Gln Lys Leu Gln Gln Trp
1               5                   10                  15

Tyr Arg Glu His Arg Ser Glu Leu Asn Leu Arg Arg Leu Phe Asp Ala
            20                  25                  30

Asn Lys Asp Arg Phe Asn His Phe Ser Leu Thr Leu Asn Thr Asn His
            35                  40                  45

Gly His Ile Leu Val Asp Tyr Ser Lys Asn Leu Val Thr Glu Asp Val
        50                  55                  60

Met Arg Met Leu Val Asp Leu Ala Lys Ser Arg Gly Val Glu Ala Ala
65                  70                  75                  80

Arg Glu Arg Met Phe Asn Gly Glu Lys Ile Asn Tyr Thr Glu Gly Arg
                85                  90                  95

Ala Val Leu His Val Ala Leu Arg Asn Arg Ser Asn Thr Pro Ile Leu
            100                 105                 110

Val Asp Gly Lys Asp Val Met Pro Glu Val Asn Lys Val Leu Asp Lys
            115                 120                 125

Met Lys Ser Phe Cys Gln Arg Val Arg Ser Gly Asp Trp Lys Gly Tyr
    130                 135                 140

Thr Gly Lys Thr Ile Thr Asp Val Ile Asn Ile Gly Ile Gly Gly Ser
145                 150                 155                 160

Asp Leu Gly Pro Leu Met Val Thr Glu Ala Leu Lys Pro Tyr Ser Ser
                165                 170                 175

Gly Gly Pro Arg Val Trp Tyr Val Ser Asn Ile Asp Gly Thr His Ile
            180                 185                 190

Ala Lys Thr Leu Ala Gln Leu Asn Pro Glu Ser Ser Leu Phe Ile Ile
        195                 200                 205

Ala Ser Lys Thr Phe Thr Thr Gln Glu Thr Ile Thr Asn Ala Glu Thr
    210                 215                 220

Ala Lys Glu Trp Phe Leu Gln Ala Ala Lys Asp Pro Ser Ala Val Ala
225                 230                 235                 240

Lys His Phe Val Ala Leu Ser Thr Asn Thr Thr Lys Val Lys Glu Phe
                245                 250                 255

Gly Ile Asp Pro Gln Asn Met Phe Glu Phe Trp Asp Trp Val Gly Gly
            260                 265                 270

Arg Tyr Ser Leu Trp Ser Ala Ile Gly Leu Ser Ile Ala Trp His Val
        275                 280                 285

Gly Phe Asp Asn Phe Glu Gln Leu Leu Ser Gly Ala His Trp Met Asp
    290                 295                 300

His His Phe Arg Thr Thr Pro Leu Glu Lys Asn Ala Pro Val Leu Leu
305                 310                 315                 320

Ala Leu Leu Gly Ile Trp Tyr Ile Asn Cys Leu Trp Gly Cys Glu Thr
                325                 330                 335

His Ala Met Leu Pro Tyr Asp Gln Tyr Leu Gln Arg Phe Ala Ala Tyr
            340                 345                 350

Phe Gln Gln Gly Asp Leu Glu Ser Asn Gly Lys Tyr Ile Thr Lys Ser
        355                 360                 365

Gly Thr Arg Val Asp His Gln Thr Gly Pro Ile Val Trp Gly Glu Pro
    370                 375                 380

Gly Thr Asn Gly Gln His Ala Phe Tyr Gln Leu Ile His Gln Gly Thr
385                 390                 395                 400

Lys Met Ile Pro Cys Asp Phe Leu Ile Pro Val Gln Thr Gln His Pro
                405                 410                 415

Ile Arg Lys Gly Leu His His Lys Ile Leu Leu Ala Asn Phe Leu Ala
```

```
                    420                 425                 430

Gln Thr Glu Ala Leu Met Arg Gly Lys Ser Thr Glu Glu Ala Arg Lys
            435                 440                 445

Glu Leu Gln Ala Ala Gly Lys Ser Pro Glu Asp Leu Glu Arg Leu Leu
        450                 455                 460

Pro His Lys Val Phe Glu Gly Asn Arg Pro Thr Asn Ser Ile Val Phe
465                 470                 475                 480

Thr Lys Leu Thr Pro Phe Met Leu Gly Ala Leu Val Ala Met Tyr Glu
                485                 490                 495

His Lys Ile Phe Val Gln Gly Ile Ile Trp Asp Ile Asn Ser Phe Asp
            500                 505                 510

Gln Trp Gly Val Glu Leu Gly Lys Gln Leu Ala Lys Lys Ile Glu Pro
        515                 520                 525

Glu Leu Asp Gly Ser Ala Gln Val Thr Ser His Asp Ala Ser Thr Asn
    530                 535                 540

Gly Leu Ile Asn Phe Ile Lys Gln Gln Arg Glu Ala Arg Val Gln
545                 550                 555

<210> SEQ ID NO 2
<211> LENGTH: 23
<212> TYPE: DNA
<213> ORGANISM: Artificial Sequence
<220> FEATURE:
<223> OTHER INFORMATION: forward primer

<400> SEQUENCE: 2
tacatatggc cgctctcacc cgg                                              23

<210> SEQ ID NO 3
<211> LENGTH: 28
<212> TYPE: DNA
<213> ORGANISM: Artificial Sequence
<220> FEATURE:
<223> OTHER INFORMATION: reverse primer

<400> SEQUENCE: 3
gcagcgcgag gccagagtcc aactcgag                                         28

<210> SEQ ID NO 4
<211> LENGTH: 558
<212> TYPE: PRT
<213> ORGANISM: Homo sapiens

<400> SEQUENCE: 4

Met Ala Ala Leu Thr Arg Asp Pro Gln Phe Gln Lys Leu Gln Gln Trp
1               5                   10                  15

Tyr Arg Glu His Arg Ser Glu Leu Asn Leu Arg Arg Leu Phe Asp Ala
            20                  25                  30

Asn Lys Asp Arg Phe Asn His Phe Ser Leu Thr Leu Asn Thr Asn His
        35                  40                  45

Gly His Ile Leu Val Asp Tyr Ser Lys Asn Leu Val Thr Glu Asp Val
    50                  55                  60

Met Arg Met Leu Val Asp Leu Ala Lys Ser Arg Gly Val Glu Ala Ala
65                  70                  75                  80

Arg Glu Arg Met Phe Asn Gly Glu Lys Ile Asn Tyr Thr Glu Gly Arg
                85                  90                  95

Ala Val Leu His Val Ala Leu Arg Asn Arg Ser Asn Thr Pro Ile Leu
            100                 105                 110
```

-continued

```
Val Asp Gly Lys Asp Val Met Pro Glu Val Asn Lys Val Leu Asp Lys
            115                 120                 125

Met Lys Ser Phe Cys Gln Arg Val Arg Ser Gly Asp Trp Lys Gly Tyr
    130                 135                 140

Thr Gly Lys Thr Ile Thr Asp Val Ile Asn Ile Gly Ile Gly Gly Ser
145                 150                 155                 160

Asp Leu Gly Pro Leu Met Val Thr Glu Ala Leu Lys Pro Tyr Ser Ser
                165                 170                 175

Gly Gly Pro Arg Val Trp Tyr Val Ser Asn Ile Asp Gly Thr His Ile
            180                 185                 190

Ala Lys Thr Leu Ala Gln Leu Asn Pro Glu Ser Ser Leu Phe Ile Ile
        195                 200                 205

Ala Ser Lys Thr Phe Thr Thr Gln Glu Thr Ile Thr Asn Ala Glu Thr
    210                 215                 220

Ala Lys Glu Trp Phe Leu Gln Ala Ala Lys Asp Pro Ser Ala Val Ala
225                 230                 235                 240

Lys His Phe Val Ala Leu Ser Thr Asn Thr Thr Lys Val Lys Glu Phe
                245                 250                 255

Gly Ile Asp Pro Gln Asn Met Phe Glu Phe Trp Asp Trp Val Gly Gly
            260                 265                 270

Arg Tyr Ser Leu Trp Ser Ala Ile Gly Leu Ser Ile Ala Leu His Val
        275                 280                 285

Gly Phe Asp Asn Phe Glu Gln Leu Leu Ser Gly Ala His Trp Met Asp
    290                 295                 300

Gln His Phe Arg Thr Thr Pro Leu Glu Lys Asn Ala Pro Val Leu Leu
305                 310                 315                 320

Ala Leu Leu Gly Ile Trp Tyr Ile Asn Cys Phe Gly Cys Glu Thr His
                325                 330                 335

Ala Met Leu Pro Tyr Asp Gln Tyr Leu His Arg Phe Ala Ala Tyr Phe
            340                 345                 350

Gln Gln Gly Asp Met Glu Ser Asn Gly Lys Tyr Ile Thr Lys Ser Gly
        355                 360                 365

Thr Arg Val Asp His Gln Thr Gly Pro Ile Val Trp Gly Glu Pro Gly
    370                 375                 380

Thr Asn Gly Gln His Ala Phe Tyr Gln Leu Ile His Gln Gly Thr Lys
385                 390                 395                 400

Met Ile Pro Cys Asp Phe Leu Ile Pro Val Gln Thr Gln His Pro Ile
                405                 410                 415

Arg Lys Gly Leu His His Lys Ile Leu Leu Ala Asn Phe Leu Ala Gln
            420                 425                 430

Thr Glu Ala Leu Met Arg Gly Lys Ser Thr Glu Glu Ala Arg Lys Glu
        435                 440                 445

Leu Gln Ala Ala Gly Lys Ser Pro Glu Asp Leu Glu Arg Leu Leu Pro
    450                 455                 460

His Lys Val Phe Glu Gly Asn Arg Pro Thr Asn Ser Ile Val Phe Thr
465                 470                 475                 480

Lys Leu Thr Pro Phe Met Leu Gly Ala Leu Val Ala Met Tyr Glu His
                485                 490                 495

Lys Ile Phe Val Gln Gly Ile Ile Trp Asp Ile Asn Ser Phe Asp Gln
            500                 505                 510

Trp Gly Val Glu Leu Gly Lys Gln Leu Ala Lys Lys Ile Glu Pro Glu
        515                 520                 525

Leu Asp Gly Ser Ala Gln Val Thr Ser His Asp Ala Ser Thr Asn Gly
```

```
                530                 535                 540
Leu Ile Asn Phe Ile Lys Gln Gln Arg Glu Ala Arg Val Gln
545                 550                 555
```